United States Patent [19]

Berman

[11] Patent Number: 4,735,214

[45] Date of Patent: Apr. 5, 1988

[54] GASTROINTESTINAL DIAGNOSTIC CAPSULE AND METHOD OF USE

[76] Inventor: Irwin R. Berman, 2301 Parkwood Dr., Brunswick, Ga. 31520

[21] Appl. No.: 903,769

[22] Filed: Sep. 5, 1986

[51] Int. Cl.⁴ ............................................. A61B 10/00
[52] U.S. Cl. .................................... 128/759; 128/769
[58] Field of Search ........................................ 128/4–8, 128/631, 638, 749, 756–759, 762, 769

[56] References Cited

U.S. PATENT DOCUMENTS

| | | | |
|---|---|---|---|
| 3,217,705 | 11/1965 | Billings | 128/638 |
| 3,688,763 | 9/1972 | Cromarty | 128/769 |
| 3,842,166 | 10/1974 | Bucalo | 128/749 |
| 3,877,464 | 4/1975 | Vermes | 128/759 |
| 4,186,730 | 2/1980 | Bucalo | 128/769 |
| 4,227,537 | 10/1980 | Suciu et al. | 128/756 |
| 4,361,948 | 12/1982 | Omata | 128/756 |
| 4,465,072 | 8/1984 | Taheri | 128/756 |
| 4,481,952 | 11/1984 | Paulec | 128/769 |
| 4,485,824 | 12/1984 | Koll | 128/756 |
| 4,586,604 | 5/1986 | Alter | 128/756 |

*Primary Examiner*—Max Hindenburg
*Attorney, Agent, or Firm*—Fleit, Jacobson, Cohn & Price

[57] ABSTRACT

A gastrointestinal diagnostic capsule that includes an encapsulated expandable foam material introduced through the oral cavity and through the esophagus into the stomach with the capsule being dissolved by the temperature and moisture conditions encountered so that the foam block or cube can expand in the stomach and be withdrawn through the gastroesophageal junction and up through the entire esophagus to obtain specimen material for diagnostic procedures for early detection of gastroesophageal cancer. The capsule and encapsulated expandable body or block of foam material which has been reduced in volume before encapsulation includes a flexible cord connected thereto and is preferably introduced on the end of a nasogastric tube, endoscope or stylus device to enable accurate positioning of the capsule after which the introducer or nasogastric tube may be withdrawn so that when the abrasive foam body or block has expanded in the stomach, it may be withdrawn through the gastroesophageal junction and up through the entire esophagus with the abrasive foam blocking obtaining cellular specimens for subsequent processing and cytology to enable ready detection of gastroesophageal cancer. Similar insertion and withdrawal techniques with the diagnostic capsule introduced through the anus by using a colonoscope allows early detection by cytology of colon cancer in patients with chronic ulcerative colitis.

8 Claims, 1 Drawing Sheet

U.S. Patent    Apr. 5, 1988    4,735,214
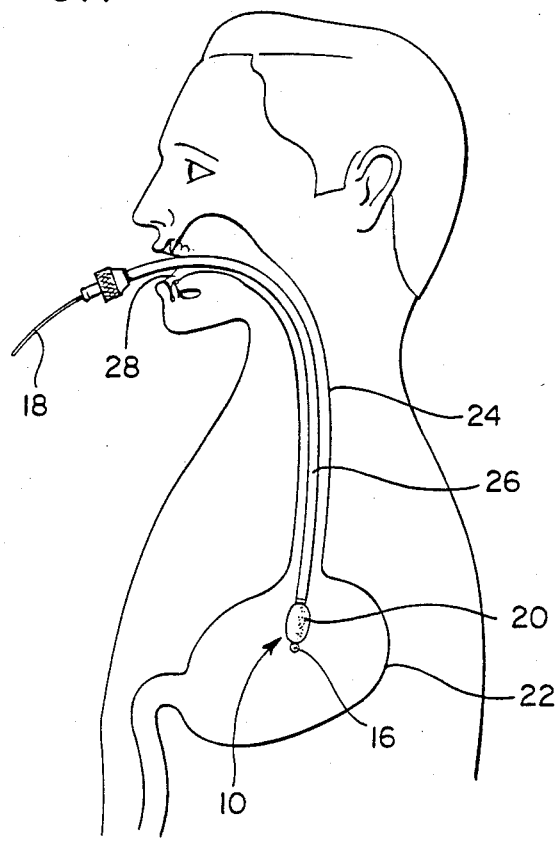
FIG. 1
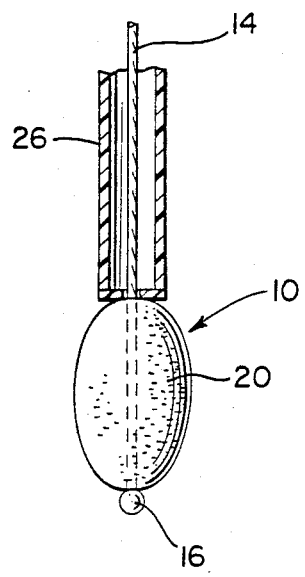
FIG. 2
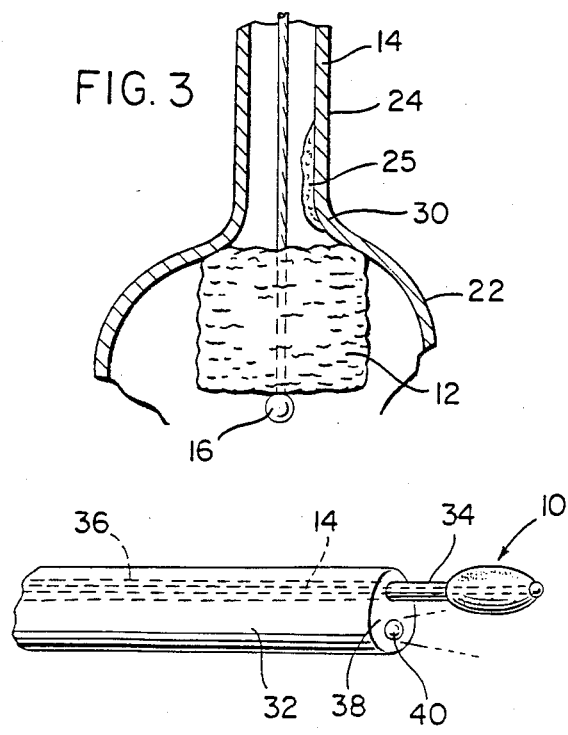
FIG. 3
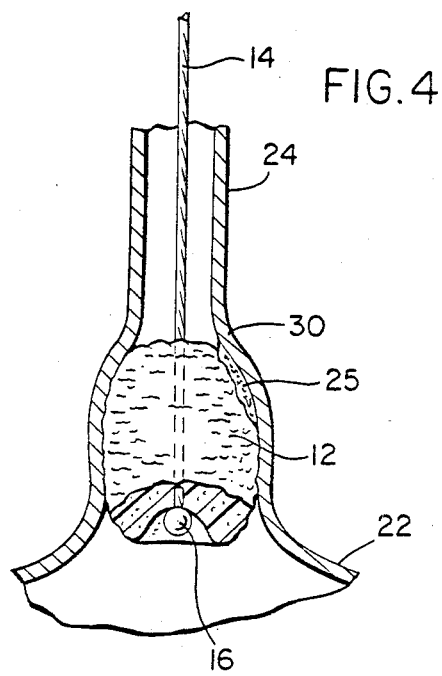
FIG. 4
FIG. 5

GASTROINTESTINAL DIAGNOSTIC CAPSULE AND METHOD OF USE

BACKGROUND OF THE INVENTION

1. Field of the Invention

The present invention generally relates to a gastrointestinal diagnostic capsule that includes an encapsulated expandable foam material introduced through the oral cavity and through the esophagus into the stomach with the capsule being dissolved by the temperature and the moisture conditions encountered in the stomach so that the foam block or cube can expand and be withdrawn through the gastroesophageal junction and up through the entire esophagus to obtain specimen material for diagnostic procedures for early detection of gastroesophageal cancer. The capsule and encapsulated expandable body or block of foam material which has been reduced in volume before encapsulation includes a flexible cord connected thereto and is preferably introduced on the end of a nasogastric tube, gastroscope or other appropriate stylus device to enable accurate positioning of the capsule after which the introducer or nasogastric tube may be withdrawn so that when the abrasive foam body or block has expanded in the stomach, it may be withdrawn through the gastroesophageal junction and up through the entire esophagus with the large exposed pore surface area of the abrasive foam block obtaining cellular specimens for subsequent processing and cytology to enable ready detection of gastroesophageal cancer.

2. Information Disclosure Statement

Esophageal cancer, once established, is almost uniformly fatal. Accordingly, early detection of gastroesophageal cancer is quite important in altering the lethality of the disease and it is generally assumed that unless esophageal cancer is detected at the epithelial or surface stage, the lethality cannot be altered. Techniques for early diagnosis of esophageal cancel involve the use of frequent endoscopy which has substantial limitations due to its reliance on inspection or random biopsy. Some efforts have been made to obtain specimen material for cytology by utilizing an inflatable balloon covered with a fishnet type of material which is stretched when the balloon is inflated so that it will abrade the esophagus during withdrawal which necessitates the introduction of the balloon into the stomach or esophagus when uninflated and subsequently the balloon must be inflated with extreme care being necessary to monitor the degree of inflation so that an appropriate abrading action on the esophagus can be obtained when the inflated balloon is withdrawn without the balloon being over inflated and causing esophagus trauma. Moreover, the fishnet pore surface area is substantially reduced due to the relatively large void spaces between the strands of the fishnet.

The incidence of gastroesophageal cancer varies considerably in different geographical areas. In those areas having a very high incidence of esophageal cancer such as the Far East, Scandinavia and to some extent in Puerto Rico, frequent endoscopy is performed in an attempt to accomplish early detection and postoperative monitoring of esophageal cancer. While the incidence of esophageal cancer in the United States is relatively low, esophageal cancer is everywhere considered almost uniformly lethal, due partly to proximity of the esophagus to vital structures that cannot be readily resected in a cancer operation and also being partly due to failure of early detection. Thus, while early detection and monitoring is recognized as a necessity in the reduction of lethality of esophageal cancer, the techniques for such detection remain relatively primitive and have not been effective in early detection of the disease except as cited with the fishnet balloon device.

SUMMARY OF THE INVENTION

An object of the present invention is to provide a gastrointestinal diagnostic capsule including an encapsulated enpandable foam device capable of passage through the esophagus into the stomach at the end of a nasogastric tube, stylus device, an endoscope, a gastroscope or conceivably swallowed, with the capsule being left in the stomach while the introducer is withdrawn with the gelatin or otherwise composed or fabricated capsule being dissolved so that the reduced volume foam can expand into an abrasive foam block in the stomach with the abrasive foam block then being withdrawn through the gastroesophageal junction and up through the entire esophagus with the collected specimen being subsequently processed cytologically such as by using a "pap" smear technique conventionally employed for detecting cervical cancer.

Another object of the invention is to provide a gastrointestinal diagnostic capsule in accordance with the preceding object which includes a capsule with a reduced volume foam material encapsulated therein and a flexible tension cord connected thereto so that the capsule can be inserted through the esophagus into the stomach so that dissolution of the capsule enables expansion of the foam material into an abrasive foam block having a large exposed pore surface area which will effectively obtain and entrap cellular material from the esophagus during withdrawal so that esophageal cancer can be detected by conventional smear tests thereby facilitating early detection and postoperative monitoring of esophageal cancer and thus reducing the lethality thereof.

A further object of the invention is to provide a gastrointestinal diagnostic capsule in accordance with the preceding objects in which the capsule is constructed of soft synthetic or gelatinous material so that little resistance would occur to passage of the capsule through the esophagus during insertion with the capsule being preferably inserted by using a nasogastric tube, stylus, endoscope or gastroscope having the cord threaded therethrough so that the cord tension will maintain the capsule properly located at the end of the nasogastric tube, stylus or endoscope during insertion and enabling withdrawal of the expanded foam thereby enabling a relatively simple technique to be used to obtain cellular specimens from the esophagus for early detection and postoperative monitoring of esophageal cancer.

A further object of the invention is to provide a gastrointestinal diagnostic capsule in accordance with the preceding objects in which the flexible tension cord passes through the body of the encapsulated foam and is secured at its most remote aspect with a retention bead or other retention configuration that is metallic, radiopaque or otherwise visible on fluoroscopic or X-ray examination with the retention bead also facilitating withdrawal of the device by effecting compression of the foam block during withdrawal.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a schematic illustration of the gastrointestinal diagnostic capsule of the present invention illustrating the manner in which it is inserted through the mouth, esophagus and into the stomach.

FIG. 2 is an enlarged fragmental sectional view illustrating the association of the capsule, tension cord connected thereto and the nasogastric tube.

FIG. 3 is a sectional view similar to FIG. 2 but illustrating the encapsulated foam block in expanded condition located at the gastroesophageal junction in position for withdrawal through the esophagus.

FIG. 4 is a fragmental sectional view similar to FIG. 3 but illustrating the foam block being withdrawn through the esophagus.

FIG. 5 is a fragmental perspective view of the present invention associated with an endoscope.

DESCRIPTION OF THE PREFERRED EMBODIMENT

Referring now specifically to the drawings, the gastrointestinal diagnostic capsule of the present invention is generally designated by reference number 10 and includes a block or cube of expandable, resilient, soft foam plastic material 12 such as a substantially hydrophilic, closed cell, polyurethane foam which, in its fully expanded state, may be cubical, cylindrical or of other predetermined shape having a predetermined size adapting it for its specific use. A tension cord or string 14 having size and strength characteristics required for its use such as a nylon cord is connected to the foam material 12 by it passing therethrough and having one end provided with an X-ray visible or radiopaque traction bead or enlargement 16 which will engage the surface of the foam material in remote relation to the free end 18 of the cord so that when tension force is exerted on the cord, the cord will not pull through the foam material and the foam material can compress somewhat during withdrawal.

The foam material 12 is compressed and encapsulated in a capsule 20 of gelatin, synthetic or similar material capable of being dissolved by body warmth and moisture. The capsule may be coated with a coating which may not dissolve in saliva but quickly dissolves in the acidic environment in the stomach or the capsule may be constructed entirely of acid sensitive material which will maintain its integrity in the mouth and esophagus but quickly disintegrate in the stomach. As illustrated in FIG. 2, the capsule 20 is generally oval-shaped or egg-shaped in configuration with the traction bead 16 oriented at one end thereof and externally of the capsule 20 with the cord 14 extending from the capsule 20 at the opposite end thereof.

As illustrated in FIG. 1, the diagnostic capsule 10 is preferably inserted into the stomach 22 through the esophagus 24 by utilizing a nasogastric tube 26, endoscope or stylus through which the cord 14 has been threaded so that the cord under tension is used to retain the capsule 20 against the distal end of the nasogastric tube 26, endoscope or stylus to facilitate insertion of the capsule 20 along with the cord 14 in through the mouth 28 and downwardly through the esophagus 24 into the stomach 22 with the capsule 20 being left in the stomach and the nasogastric tube 26 or other introducer then being withdrawn from the stomach, esophagus and mouth. After the capsule 20 has dissolved and the foam plastic 12 expanded into the condition illustrated in FIG. 3, the foam block can be moved into contact with and withdrawn through the gastroesophageal junction 30 and up through the esophagus 24. Due to the soft resilient characteristics of the foam plastic 12 and to the retention bead 16, the foam plastic will reduce slightly in diameter and be deformed so that the upper surface thereof is rounded into a generally convex shape whereas the trailing surface will be generally concave. While it is preferable to remove the introducer tube, stylus or endoscope prior to withdrawal of the expanded foam plastic device, it is also possible to utilize the tube 26, stylus or endoscope during withdrawal in order to provide greater visibility or more positive control of movement of the foam plastic 12 as it is withdrawn through the esophagus 24. The soft foam material has some degree of porosity and is substantially non-absorbent and will collect and retain material abraded from an early cancer 25 that may exist on the interior of the esophagus 24, as shown in FIGS. 3 and 4 due to the pores having their peripheral edges forming the large exterior surface which provide abrasive characteristics to the cellular formation of the foam plastic.

FIG. 5 illustrates an arrangement in which the diagnostic capsule 10 and tension cord 14 are associated with an endoscope 32 to provide and maintain visibility during insertion and possibly during withdrawal. In this arrangement, the tension cord 14 is threaded and held through a catheter 34 which includes a polyethylene tube positioned through the endoscope channel 36 in which the capsule 10 is held several centimeters ahead of the tip 38 of the endoscope which also includes an illumination device 40 thereon.

While the drawings and previous description relate to early detection of esophageal cancer, the invention is also useful in association with other body orifices or hollow organs. In this regard, the device may be passed into the gastrointestinal tract or other orifice, such as the colon or vagina, either manually or by using an introducer such as the nasogastric tube disclosed, rectal tube, or the like or an endoscope including a flexible gastroscope or colonoscope. By threading the tension cord 14 through the catheter 34 in the endoscope channel 36, the capsule 10 may be held several centimeters ahead of the endoscope tip 38 during insertion. Once the capsule has been placed at the desired position in the desired hollow organ, expansion will occur in place and the expanded abrasive foam is then withdrawn, possibly under direct vision with the endoscope, by using the attached cord 14 which is threaded through the catheter and connected through the foam plug and secured with the traction bead which is preferably metallic or otherwise radiopacque to show on X-rays. The bead, being located at the most internal aspect of the foam plastic, will cause the foam plastic periphery to conform with, flex but yet resiliently engage the surface of the hollow organ through which it is pulled. After withdrawal of the expanded foam body, cellular specimen material is then removed or extracted from the foam or an imprint of the foam can be made on a slide for appropriate cellular analysis by microscopic cytology and histology techniques conventionally available for cellular materials and tissues.

In these instances and uses, especially when the capsule is passed by swallowing, the capsule may dissolve too early causing premature rupture of the capsule and expansion of the foam body which may in some instances cause the illusion of strangulation if expansion occurs in the mid to upper portion of the esophagus. Thus, the capsule may be coated or otherwise composed or fabricated to provide its predictable passage in all instances into the stomach before opening although by using an endoscope or introducer, the capsule usually can be inserted and accurately positioned before dissolution. The capsule 20 is preferably the same size as the largest size medicinal capsule so that it can pass through the esophagus without difficulty and without injury or discomfort to the patient. The tension cord 14 preferably has a length ranging between 25-30 inches at least and the expanded foam block is generally cylindrical or ovoid with a diameter and length of approximately 2 inches so that it can deform when being moved outwardly as shown in FIG. 4 and still effectively abrade and collect cellular material in the pores during withdrawal.

In addition to detection of esophageal carcinoma, the invention may be also especially useful in early detection of colon cancer. By using this invention in patients with chronic ulcerative colitis, abrasion of the entire length of the colon allows more accurate early diagnosis than provided by regular endoscopic examination and random biopsies. Early diagnosis of colon cancer in chronic ulcerative colitis is of major significance since detection of cancerous cells anywhere in the colon in ulcerative colitis usually mandates total removal of the colon and rectal lining. Regardless of how the capsule is inserted into the body orifice or cavity, the essential function to be accomplished is the in-situ expansion of the foam cube, block or body and subsequent withdrawal thereof with the soft resilient characteristics of the expanded foam and the abrasive characteristics of the external porous surface thereof effectively removing, collecting and retaining cellular material from the internal peripheral surfaces of the body orifice or cavity so that such material may be subsequently cytologically analyzed for early detection of cancer and other diseases capable of being detected by this procedure.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A diagnostic device for obtaining cellular material from the interior of a body orifice or cavity comprising a body of soft, resilient, expandable and compressible porous foam material having an exterior abrading surface, a flexible cord attached to said body and a capsule encapsulating the body of foam material and retaining it in a compressed small volume condition for manual insertion into the body orifice or cavity, said capsule being constructed of material dissolved by body warmth and moisture or acidity to enable the foam material to expand in-situ to a predetermined size and shape for removing cellular material from the interior surface of the body orifice or cavity as the body of foam material is manually withdrawn from the body orifice or by cord tensioning cavity while in resilient friction contact therewith to abrade and remove material for cytological analysis for early detection of cancer cells and the like.

2. The device as defined in claim 1 together with an elongated flexible introducer receiving the cord therethrough and engaging the capsule to enable the capsule to be positioned in a predetermined location in the body orifice or cavity.

3. The device as defined in claim 1 wherein said cord extends through the body of foam material and includes an enlargement on the end thereof distal from the free end of the cord to engage the foam material to prevent the cord from pulling through the foam material when tension is exerted thereon and to allow the foam material to compress somewhat during withdrawal.

4. The device as defined in claim 3 wherein said enlargement includes a metallic or otherwise radiopaque bead or enlargement capable of observation by X-ray techniques in order to facilitate precise localization of the device prior to withdrawal.

5. The device as defined in claim 2 wherein said introducer is a nasogastric tube.

6. The device as defined in claim 2 wherein said introducer is an endoscope, gastroscope, colonoscope or stylus device.

7. The device as defined in claim 2 wherein said introducer is a nasogastric tube, endoscope, or stylus device for inserting the capsule into the stomach through the esophagus with the introducer then being capable of being removed and after expansion of the foam plastic in situ, withdrawal of the foam plastic by tensioning and pulling the cord will abrade and remove cellular specimen material from the esophagus for use in early detection of esophageal cancer.

8. The method of obtaining cellular specimen material from the interior of the esophagus for cytological analysis for detection of cancer cells and the like consisting of the steps of manually inserting a body of compressed foam material having a cord attached thereto and encapsulated in a dissolvable capsule through the esophagus into the stomach by using a flexible introducer tube with the cord extending through the tube for tensioning to hold the capsule against the end of the tube during insertion, removing the tube, permitting the capsule to dissolve and the body of foam material to expand in the stomach and manually removing the body of foam material by pulling the cord to move the body of material from the stomach into the gastroesophageal junction and through the esophagus while in resilient friction contact therewith to abrade and remove material for cytological analysis.

* * * * *